(12) United States Patent
Denissen (10) Patent No.: US 9,925,012 B2
(45) Date of Patent: Mar. 27, 2018

(54) ROBOTIC SYSTEM

(71) Applicant: KONINKLIJKE PHILIPS N.V., Eindhoven (NL)

(72) Inventor: Sander Hans Denissen, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 33 days.

(21) Appl. No.: 14/911,741

(22) PCT Filed: Aug. 21, 2014

(86) PCT No.: PCT/EP2014/067788
§ 371 (c)(1),
(2) Date: Feb. 12, 2016

(87) PCT Pub. No.: WO2015/032625
PCT Pub. Date: Mar. 12, 2015

(65) Prior Publication Data
US 2016/0184038 A1    Jun. 30, 2016

(30) Foreign Application Priority Data
Sep. 4, 2013  (EP) .................................... 13182929

(51) Int. Cl.
*B25J 9/16* (2006.01)
*A61B 34/30* (2016.01)
(Continued)

(52) U.S. Cl.
CPC .............. *A61B 34/30* (2016.02); *A61B 34/32* (2016.02); *B25J 9/1633* (2013.01);
(Continued)

(58) Field of Classification Search
CPC ......... A61B 34/30; A61B 34/32; A61B 34/20; A61B 2034/107; A61B 2034/2061;
(Continued)

(56) References Cited

U.S. PATENT DOCUMENTS

| 7,772,541 B2 | 8/2010 | Froggatt et al. | |
| 2007/0027579 A1* | 2/2007 | Suzuki ................ | G05D 1/0251 700/245 |

(Continued)

*Primary Examiner* — Abby Y Lin (57) ABSTRACT

The invention relates to a robotic system for moving a shapeable instrument like a shapeable catheter within an object like a person. The system (1) comprises a robotic device (2, 3) for modifying the shape of the instrument (2) and moving the instrument within the object (7) and a control unit (4) for controlling the robotic device based on structure information like a roadmap, a target position and shape and an actual position and shape such that the instrument is moved and the shape of the instrument is modified from the actual position and shape to the target position and shape. Since the control unit considers structure information while controlling the robotic device, the navigation of the instrument can be automatically performed under consideration of knowledge about regions within the object, through which the instrument is navigatable. The navigation may therefore be performed without or with few user interactions only.

14 Claims, 3 Drawing Sheets

(51) Int. Cl.
*A61B 34/32* (2016.01)
*A61B 17/00* (2006.01)
*A61B 90/00* (2016.01)
*A61B 34/10* (2016.01)
*A61B 34/20* (2016.01)

(52) U.S. Cl.
CPC ... *A61B 2017/003* (2013.01); *A61B 2034/107* (2016.02); *A61B 2034/2061* (2016.02); *A61B 2034/301* (2016.02); *A61B 2090/3782* (2016.02); *G05B 2219/40074* (2013.01); *G05B 2219/40418* (2013.01); *G05B 2219/45118* (2013.01); *Y10S 901/02* (2013.01); *Y10S 901/09* (2013.01)

(58) Field of Classification Search
CPC ...... A61B 2034/301; A61B 2090/3782; A61B 2017/003; A61B 5/065; A61B 5/06852; G05B 2219/40074; G05B 2219/40418; G05B 2219/45118; Y10S 901/02; Y10S 901/09; A61M 2025/1066; A61M 25/0133; A61M 25/014
See application file for complete search history.

(56) References Cited

U.S. PATENT DOCUMENTS

| | | |
|---|---|---|
| 2010/0249506 A1 | 9/2010 | Prisco |
| 2011/0319714 A1 | 12/2011 | Roelle et al. |
| 2011/0319815 A1 | 12/2011 | Roelle et al. |
| 2012/0132009 A1 | 5/2012 | Prisco |
| 2013/0085334 A1 | 4/2013 | Ramamurthy et al. |
| 2013/0269109 A1 | 10/2013 | Yu |
| 2013/0304258 A1* | 11/2013 | Taylor ............... 700/260 |
| 2013/0310685 A1 | 11/2013 | Chan et al. |
| 2016/0324587 A1* | 11/2016 | Olson ............ A61B 34/32 |

* cited by examiner

ROBOTIC SYSTEM

CROSS-REFERENCE TO PRIOR APPLICATIONS

This application is the U.S. National Phase application under 35 U.S.C. § 371 of International Application Serial No. PCT/EP2014/067788, filed on Aug. 21, 2014, which claims the benefit of European Patent Application No. 13182929.3, filed on Sep. 4, 2013.

These applications are hereby incorporated by reference herein.

FIELD OF THE INVENTION

The invention relates to a robotic system, a robotic method and a computer program for moving a shapeable instrument within an object.

BACKGROUND OF THE INVENTION

If a medical robotic system for navigating a shapeable interventional instrument within a person, in particular, within a vessel of the person, like the Magellan robotic system from the company Hansen is used by a physician, the physician has to control the medical robotic system such that the interventional instrument reaches a desired target region within the person. This control of the medical robotic system requires a lot of user interactions, which makes the interventional procedure relatively cumbersome for the physician.

The US 2011/0319815 A1 discloses a fiber optic instrument sensing system that improves control of a shapeable or steerable instrument using shape data. Additional systems use such shape data for improved mapping or adjusting models of the instrument. Such systems include robotic medical systems for controlling a shapeable instrument within an anatomical region having a controller, one or more actuators, and a localization system for guiding one or more shapeable instruments.

SUMMARY OF THE INVENTION

It is an object of the present invention to provide a robotic system, a robotic method and a computer program for moving a shapeable instrument within an object, which allow for a reduction of user interactions while navigating the shapeable instrument within the object.

In a first aspect of the present invention a robotic system for moving a shapeable instrument within an object is presented, wherein the system comprises:

a robotic device for modifying the shape of the instrument and moving the instrument within the object, an inner structure providing unit for providing structure information about the inner structure of the object, a target position and shape providing unit for providing a target position and shape of the instrument within the object, an actual position and shape providing unit for providing the actual position and shape of the instrument within the object, a control unit for controlling the robotic device based on the structure information, the target position and shape of the instrument and the actual position and shape of the instrument such that the instrument is modified and moved from the actual position and shape to the target position and shape, wherein the inner structure providing unit is further adapted to indicate safety zones within the inner structure, in which the robotic device should not apply forces for modifying the shape of the instrument and/or moving the instrument within the object, which are larger than a predefined force value, wherein the control unit is adapted to control the robotic device such that no forces are applied in the safety zones being larger than the predefined force value, while the shape of the instrument is modified and the instrument is moved from the actual position and shape to the target position and shape.

Since the control unit considers the structure information while controlling the robotic device, the navigation of the instrument within the object from the actual position and shape of the instrument to the target position and shape of the instrument can be automatically performed under consideration of knowledge about regions within the object, through which the instrument is navigatable. The navigation of the instrument within the object can therefore be performed with less user interactions, in particular, without any user interaction.

The object is preferentially a living object like a person or an animal and the shapeable instrument is preferentially an interventional instrument for performing an interventional procedure. For instance, the shapeable instrument is a shapeable catheter, in particular, a shapeable microcatheter, a shapeable needle, a shapeable endoscope or any other type of shapeable medical device.

The robotic device and the instrument can be integrated such that the instrument comprises several portions, which are connected by hinges such that the portions are pivotable with respect to each other by the robotic device by using, for instance, wires, which can be connected to motors of the robotic device for allowing the motors to change the shape of the instrument. The robotic device can comprise at least two further motors for translating the entire instrument and for rotating the entire instrument. In particular, for translating and rotating the entire instrument the robotic device may comprise a mechanical fixture for clamping the instrument, wherein the at least two further motors may be adapted to translate the mechanical fixture along a rail and to rotate the mechanical fixture. The robotic device may also be configured such that the instrument is rotated within the mechanical fixture by using at least one of the further motors. The motors of the robotic device may be controlled by the control unit, in order to modify the shape of the instrument and move the instrument based on the structure information, the target position and shape of the instrument and the actual position and shape of the instrument.

The inner structure providing unit can be a storing unit, in which the structure information is stored already and from which the structure information can be retrieved for providing the same. However, the inner structure providing unit can also be adapted to determine the structure information based on, for instance, an image of the object like a computed tomography image or a magnetic resonance image which may be acquired before the instrument is introduced into the object and/or after the instrument has been introduced into the object, i.e. pre- and/or intra-procedural, or the structure information can directly be the image of the object, which may be regarded as being a structure image. In particular, the inner structure providing unit can be adapted to generate a roadmap based on an image of the object and to provide this roadmap as the structure information, wherein the roadmap defines inner paths of the object, along which the instrument is movable.

The predefined force value can be zero indicating that no force should be applied in the safety zones. The safety zones are, for instance, zones close to the inner walls of the object or areas of high tortuosity. This allows automatically or semi-automatically navigating the instrument within the object with increased caution, thereby decreasing the likelihood of unwanted damages of the inner structure.

The target position and shape providing unit can be a storing unit, in which the target position and shape is stored already and from which the target position and shape can be retrieved for providing the same. However, the target position and shape providing unit can also be adapted to determine the target position and shape of the instrument within the object based on, for instance, the provided structure information and to provide the determined target position and shape.

The robotic system may further comprise a target region providing unit for providing a target region to which the instrument is to be moved, wherein the target position and shape providing unit may be adapted to determine the target position and shape of the instrument within the object based on the target region and the structure information. In particular, the target region providing unit may be adapted to allow a user to input the target region. For instance, the target region providing unit can be adapted to allow a user to input target landmarks like target rings, wherein the target position and shape providing unit can be adapted determine the target position and shape depending on the input target landmarks or target rings and the structure information. In particular, the user may just input, to which location the instrument should be moved, whereupon the target position and shape providing unit determines the target position and shape accordingly and the control unit controls the robotic device such that the input location is reached by the instrument. The target position and shape providing unit may be further adapted to allow the user to modify the target position and shape of the instrument.

The target position and shape providing unit can be adapted to provide target rules defining positions and shapes of the instrument depending on structure information and optionally on further features like a target region and to determine the target position and shape of the instrument depending on the structure information, the optional further features and on the target rules. The target rules can define, for instance, that the instrument should be perpendicular to an inner ring structure through which the instrument is to be navigated, that the instrument should have a certain distance to inner walls of the object, that in certain zones within the object, which may be indicated in the structure information, strong forces should not be applied, et cetera. The target position and shape can be determined such that these conditions are fulfilled.

In an embodiment the inner structure providing unit is adapted to provide a structure image, which shows the inner structure, as the structure information and the target position and shape providing unit is adapted to a) allow a user to add markers to the structure image and b) determine the target position and shape of the instrument within the object based on the added markers. This allows the user to determine the target position and shape, wherein then the control unit can, especially automatically, control the robotic device such that the instrument is positioned and shaped in accordance with the user-determined target position and shape. For example, a user may add several markers, which can be automatically connected by the target position and shape providing unit for determining the target position and shape.

The structure image may be any image showing the inner structure of the object like a magnetic resonance image, a computed tomography image, an ultrasound image or any other medical image showing the inner structure of the object. The structure image can also be an image, which shows the inner structure and which is derived from a medical image, like a roadmap derived from, for instance, a computed tomography image or a magnetic resonance image.

In a further embodiment the actual position and shape providing unit and the control unit are adapted to provide a feedback loop during a movement of the instrument within the object, wherein the actual position and shape of the instrument is continuously updated and the robotic device is continuously controlled based on the structure information, the target position and shape of the instrument and the updated actual position and shape of the instrument. Thus, it can be continuously reacted on the actual position and shape of the instrument, which may be different to what would be expected in view of the intended position and shape of the instrument because of, for instance, inaccuracies in steering the instrument. A correction loop can therefore be provided, which leads to a more accurate navigation of the instrument within the object.

In an embodiment, alternatively or in addition, the inner structure providing unit and the control unit can be adapted to provide a feedback loop during a movement of the instrument within the object, wherein the inner structure of the object is continuously updated and the robotic device is continuously controlled based on the updated structure information, the target position and shape of the instrument and the actual position and shape of the instrument. This allows the control unit to consider changes of the inner anatomy of the object, which may be caused by the instrument within the object, during the interventional procedure. Also this leads to a correction loop, which can allow for a more accurate navigation of the instrument within the object.

It is preferred that the control unit is adapted to a) determine a position and shape plan defining a modification of the shape and a movement of the instrument, which is required for arranging the instrument in accordance with the target position and shape, depending on the structure information, the target position and shape of the instrument and the actual position and shape of the instrument, and b) control the robotic device in accordance with the determined position and shape plan. The position and shape plan may explicitly or implicitly define translations and/or rotations of the entire instrument and/or of portions of the instrument. For instance, rotations between different portions of the instrument and translations and/or rotations of the entire instrument can be defined by the position and shape plan for defining a modification of the shape and a movement of the instrument, which is required for arranging the instrument in accordance with the target position and shape.

In an embodiment the inner structure providing unit is adapted to provide a structure image, which shows the inner structure, as the structure information, wherein element weights are assigned to elements of the structure image, wherein the control unit is adapted to determine the position and shape plan such that a plan weight, which depends on the element weights assigned to the elements of the structure image that correspond to regions within the object at least temporarily occupied by the instrument when performing the position and shape plan, is optimized. For instance, the plan weight can be the sum of the element weights assigned to the elements of the structure image that correspond to regions within the object at least temporarily occupied by the instrument when performing the position and shape plan. The elements of the structure image are preferentially voxels, wherein the structure image may be a roadmap, a computed tomography image, a magnetic resonance image, an image showing a model of the inner structure, et cetera.

The control unit may be adapted to determine several position and shape plans, wherein the system may further comprise a display for displaying the determined position and shape plans together with the inner structure of the object as defined by the provided structure information and wherein the control unit may be adapted to provide a user interface allowing the user to select one of the determined position and shape plans and to control the robotic device in accordance with the selected position and shape plan. Thus, a user may select a desired position and shape plan, whereupon the instrument can be automatically navigated such that it is moved and its shape is modified from the actual position and shape to the target position and shape in accordance with the selected position and shape plan.

In an embodiment the position and shape plan explicitly or implicitly defines planned intermediate positions and shapes of the instrument, which are planned to be used while the shape of the instrument is modified and the instrument is moved from the actual position and shape to the target position and shape and which correspond to translation and/or rotation steps of the entire instrument and/or of portions of the instrument for reaching the planned intermediate positions and shapes of the instrument, wherein the actual position and shape providing unit is adapted to continuously update the actual position and shape of the instrument while the shape of the instrument is modified and the instrument is moved in accordance with the position and shape plan and wherein the control unit is adapted to modify the position and shape plan, if during the modification of the shape of the instrument and the movement of the instrument in accordance with the position and shape plan a deviation between an expected planned intermediate position and shape of the instrument and the updated actual position and shape of the instrument is larger than a predefined threshold, based on the structure information, the target position and shape and the updated actual position and shape of the instrument. Thus, during the navigation process the actual position and shape of the instrument can be monitored and if the monitored actual position and shape deviates from the expected planned intermediate position and shape of the instrument, the position and shape plan can be automatically updated and the navigation process can continue in accordance with the updated position and shape plan. The modification, i.e. the updating, of the position and shape plan can be performed by re-calculating the position and shape plan based on the updated actual position and shape of the instrument, the target position and shape and the structure information.

The control unit may be adapted to allow a user to interrupt the control of the robotic device. For instance, the control unit can be adapted to control the robotic device only, if a user inputs a signal indicating that the control unit is allowed to control the robotic device based on the structure information, the target position and shape of the instrument and the actual position and shape of the instrument. In particular, the control unit can be adapted to control the robotic device only, if a switch like a hand switch or a foot switch is continuously pressed. These limited user interactions allow the user to influence the navigation procedure, wherein still the number of user interactions is relatively small.

In an embodiment the actual position and shape providing unit is adapted to provide the position and shape of the entire instrument. Considering the position and shape of the entire instrument, and not only of one or several parts of the instruments, during the navigation procedure can improve the accuracy of the navigation procedure.

The actual position and shape providing unit is preferentially adapted to provide the position and shape of the instrument by optical shape sensing (OSS). This allows providing the position and shape of the instrument with high accuracy, without requiring the user to perform cumbersome tracking procedures that may use further devices for providing, for instance, a navigation field like an electromagnetic field as needed in case of electromagnetic tracking.

In another aspect of the present invention a robotic method for moving a shapeable instrument within an object is presented, wherein the method comprises:

providing structure information about the inner structure of the object by an inner structure providing unit, providing a target position and shape of the instrument within the object by a target position and shape providing unit, providing the actual position and shape of the instrument within the object by an actual position and shape providing unit, controlling a robotic device, which is configured to modify the shape of the instrument and move the instrument within the object, based on the structure information, the target position and shape of the instrument and the actual position and shape of the instrument by a control unit such that the instrument is modified and moved from the actual position and shape to the target position and shape, indicating safety zones within the inner structure, in which the robotic device should not apply forces for modifying the shape of the instrument and/or moving the instrument within the object, which are larger than a predefined force value, and controlling the robotic device such that no forces are applied in the safety zones being larger than the predefined force value.

In a further aspect of the present invention a computer program for moving a shapeable instrument within an object is presented, wherein the computer program comprises program code means for causing a robotic system as defined in claim 1 to carry out the steps of the robotic method as defined in claim 13, when the computer program is run on a computer controlling the robotic system.

It shall be understood that the robotic system of claim 1, the robotic method of claim 13, and the computer program of claim 14 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
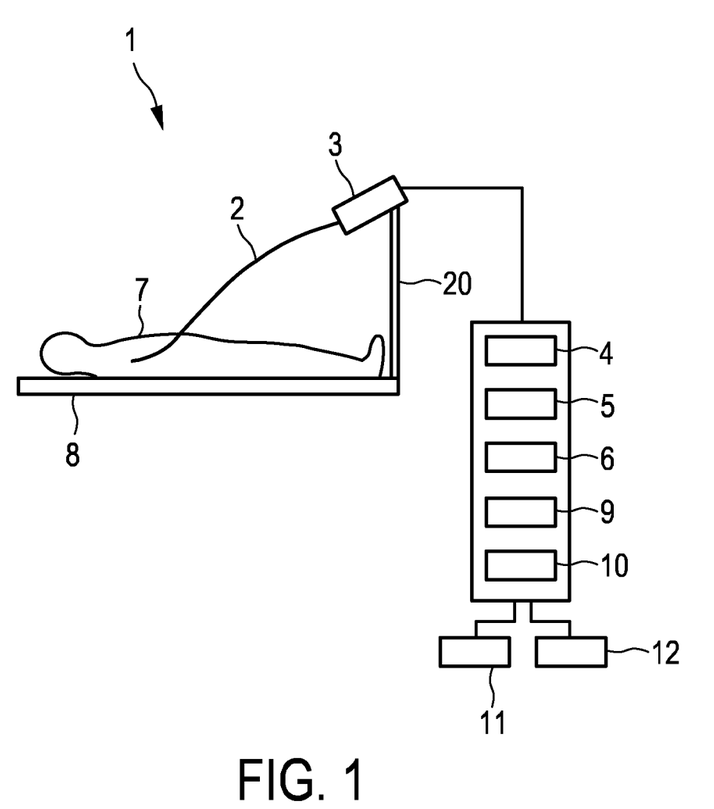
FIG. 1 shows schematically and exemplarily an embodiment of a robotic system for moving a shapeable instrument within a person, FIG. 2 schematically and exemplarily illustrates a roadmap, a target position and shape of the instrument, an actual position and shape of the instrument and target regions.

FIG. 1 shows schematically and exemplarily an embodiment of a robotic system for moving a shapeable instrument within an object. In this embodiment the robotic system 1 is adapted to move a shapeable catheter 2 within a person 7 lying on support means 8 like a patient table. The shapeable catheter 2 comprises several portions, which are connected by hinges such that the portions are pivotable with respect to each other by using wires connected to the respective portions. In particular, one end of a respective wire is connected to a respective portion of the catheter 2 and the other end of the respective wire is connected to a respective motor of a steering unit 3 such that the different portions of the catheter 2 can be pivoted with respect to each other via the wires and the motors in the steering unit 3. The steering unit 3 can be attached to the support means 8 via a rigid mechanical connection 20. The steering unit 3 comprises at least two further motors for translating the entire catheter 2 and for rotating the entire catheter 2. In particular, for translating and rotating the entire catheter 2 the steering unit 3 comprises a mechanical fixture for clamping the catheter 2, wherein the at least two further motors are adapted to translate the mechanical fixture along a rail and to rotate the mechanical fixture. As an alternative to rotating the mechanical fixture, the steering unit 3 may be configured such that the catheter 2 is rotated within the mechanical fixture by using at least one of the further motors. Generally, mechanical configurations of known robotic systems can be used for modifying the shape of the catheter and moving the catheter like the mechanical configuration of the Magellan robotic system from the company Hansen.

The steerable catheter 2 and the steering unit 3 can be regarded as forming a robotic device for modifying the shape of the catheter 2 and for moving the catheter 2 within the person 7.

The robotic system 1 further comprises an inner structure providing unit 5 for providing structure information about the inner structure of the person 7. In this embodiment the inner structure providing unit is adapted to provide a roadmap showing anatomical constraints, wherein the roadmap defines the regions within the person 7, through which the catheter 2 can be navigated. The roadmap can have been determined based on a medical image of the person 7 like a computed tomography image or a magnetic resonance image, which may have been acquired before the catheter 2 has been introduced into the person 7 or after the catheter 2 has been introduced into the person 7, i.e. the medical image can be a pre- or intra-procedural image. The inner structure providing unit 5 is further adapted to indicate safety zones within the inner structure by indicating these zones on the roadmap. The indicated safety zones define regions within the person 7, in which the robotic device 2, 3 should not apply forces for modifying the shape of the catheter 2 and/or for moving the catheter 2 within the person 7, which are larger than a predefined force value. In an embodiment the predefined force value is zero indicating that no force should be applied in the safety zones. The safety zones are, for instance, zones close to inner walls of vessels or other lumina within the person or areas of high tortuosity. The safety zones can be predefined, for instance, manually predefined. However, the safety zones can also be automatically determined by applying predefining safety rules to the roadmap, wherein the predefined safety rules can define the safety zones based on features of the inner structure like positions of inner walls within the person. For example, the safety rules can define that the safety zones are zones adjacent to inner walls of vessels or other lumina within the person 7, i.e. zones within a predefined safety distance to the inner walls. Furthermore, in an embodiment different kinds of safety zones with different safety levels can be defined, wherein to each safety level a certain force value can be predefined such that in some safety zones no forces should be applied and in other safety zones small forces are allowed.

The robotic system further comprises a target region providing unit 6 for providing a target region to which the catheter 2 is to be moved and a target position and shape providing unit 9 for providing a target position and shape of the catheter 2 within the person 7, wherein the target position and shape providing unit 9 is adapted to determine the target position and shape of the catheter 2 within the person 7 based on the target region and the roadmap. In this embodiment the target region providing unit 6 is adapted to allow a user to input the target region on the roadmap. For instance, the target region providing unit 6 can provide a graphical user interface, which allows the user to input the target region via an input unit 11 like a keyboard, a computer mouse, a touch screen, et cetera and via a display 12 showing the roadmap. The target region providing unit 6 may also be adapted to allow the user to indicate the target region on another medical image not being the roadmap like a computed tomography image or a magnetic resonance image, wherein in this case this other medical image and the roadmap are registered with respect to each other such that the location of the input target region is known with respect to the roadmap.

The target region input by the user can be a target ring enclosing a vessel opening, through which the catheter 2 should be navigated, or the target region can be another landmark. The target position and shape providing unit 9 is adapted to provide target rules defining positions and shapes of the catheter depending on structure information and depending on target regions. The target rules can define, for instance, that the catheter should be perpendicular to an inner ring structure through which the catheter is to be navigated, that the catheter should have a certain distance to inner walls of vessels or other lumina of the person, that in certain zones, i.e. the safety zones, within the person strong forces should not be applied, et cetera. The target position and shape providing unit 9 is preferentially adapted to calculate the target shape and position of the catheter 2 based on the roadmap and the input target region such that the target rules are fulfilled.

The target position and shape providing unit 9 is further adapted to allow the user to modify the target position and shape of the catheter. Thus, the target position and shape providing unit 9 can also be adapted to provide a graphical user interface allowing the user to modify the calculated target position and shape of the catheter 2 by using the input unit 11 and the display 12 on which the target position and shape may be shown together with the roadmap and/or a medical image.

The robotic system 1 further comprises an actual position and shape providing unit 10 for providing the actual position and shape of the catheter 2 within the person 7. In this embodiment the catheter 2 is equipped with an OSS fiber, which is connected to the actual position and shape providing unit 10 for providing the actual position and shape of the catheter 2 within the person 7 by using OSS. For determining the actual position and shape of the catheter 2 within the person 7 known OSS techniques can be used like the technique disclosed in U.S. Pat. No. 7,772,541 B2, which is herewith incorporated by reference. The actual position and shape providing unit 10 is adapted to provide the position and shape of the entire catheter 2 and not only of certain portions of the catheter 2.

The robotic system 1 further comprises a control unit 4 for controlling the robotic device 2, 3 based on the roadmap, the target position and shape of the catheter 2 and the actual position and shape of the catheter 2. In particular, the control unit 4 is adapted to determine a position and shape plan defining a modification of the shape and a movement of the catheter 2, which is required for arranging the catheter 2 in accordance with the target position and shape, depending on the roadmap, the target position and shape of the catheter 2 and the actual position and shape of the catheter 2 and to control the robotic device 2, 3, in particular, the motors of the steering unit 3, in accordance with the determined position and shape plan. The control unit 4 can be adapted to determine the position and shape plan by determining planned intermediate positions and shapes of the catheter 2, which are planned to be used while the shape of the catheter 2 is modified and the catheter 2 is moved from the actual position and shape to the target position and shape, wherein the actual position and shape providing unit 10 can be adapted to continuously update the actual position and shape of the catheter 2 while the shape of the catheter 2 is modified and the catheter 2 is moved in accordance with the position and shape plan and wherein the control unit 4 can be adapted to modify the position and shape plan, if during the modification of the shape of the catheter 2 and the movement of the catheter 2 in accordance with the position and shape plan a deviation between an expected planned intermediate position and shape of the catheter 2 and the updated actual position and shape of the catheter 2 is larger than a predefined threshold, based on the roadmap, the target position and shape and the updated actual position and shape of the catheter 2. Thus, the actual position and shape providing unit 10 and the control unit 4 are preferentially adapted to provide a feedback loop, while the catheter 2 is moved and the shape of the catheter 2 is modified within the person 7, wherein the actual position and shape of the catheter 2 is continuously updated and the motors of the steering unit 3 are continuously controlled based on the roadmap, the target position and shape of the catheter 2 and the updated actual position and shape of the catheter 2, wherein the position and shape plan is continuously updated based on the updated actual position and shape of the catheter 2 and the control unit 4 controls the robotic device 2, 3 in accordance with the updated position and shape plan.

The position and shape plan can define translations and rotations of the entire catheter 2 and rotations of portions of the catheter 2 with respect to each other for modifying the shape of the catheter 2 such that the planned intermediate positions and shapes and finally the target position and shape are reached. The position and shape plan can be executed by providing corresponding commands to be sent to the motors of the steering unit 3, wherein the commands prompt the motors to move and modify the shape of the catheter 2 such that the planned intermediate positions and shapes and finally the target position and shape are reached. The control unit 4 can be adapted to determine the position and shape plan based on predefined plan rules defining the position and shape plan depending on the respective target position and shape, the actual position and shape and the roadmap. For instance, the plan rules can define that, if the target region is defined by a target ring, the target ring has to be perpendicularly approached by the instrument and/or that in the safety zones no forces are allowed to be applied, which are larger than the predefined force value, in particular, that, if the force value is zero, the instrument is not allowed to be moved through the safety zones. Correspondingly, the plan rules can define that, if a sequence of target rings has been provided, the target rings have to be perpendicularly approached by the instrument and/or that in the safety zones no forces are allowed to be applied, which are larger than the predefined force value, in particular, that, if the force value is zero, the instrument is not allowed to be moved through the safety zones. The plan rules can further define that the shape modifications and the movements can only take place within the lumina indicated on the roadmap. Moreover, further possible plan rules can define that a vessel opening should be approached perpendicular to a transversal plane of the vessel opening and/or the target position and shape should be reached with a minimum number of shape modifications and movements of the catheter, et cetera.

Alternatively or in addition, element weights like risk values can be assigned to elements of the roadmap, in particular, to voxels of the roadmap, and the plan rules can define that the position and shape plan should be determined such that a plan weight, which depends on the sum of the element weights assigned to the elements of the roadmap that correspond to regions within the person 7 at least temporarily occupied by the catheter 2 when performing the position and shape plan, is optimized, particularly minimized. For instance, several position and shape plans can be determined based on plan rules defining that, if the target region is defined by a target ring, the target ring has to be perpendicularly approached by the instrument and/or that in the safety zones no forces are allowed to be applied, which are larger than the predefined force value, and/or that the shape modifications and the movements can only take place within the lumina indicated on the roadmap, and/or that a vessel opening should be approached perpendicular to a transversal plane of the vessel opening, et cetera, wherein the plan rules can further define that from these determined position and shape plans the position and shape plan is selected having the optimum plan weight, particularly having the smallest plan weight. The control unit 4 can also be adapted to allow the user to select a desired position and shape plan. In particular, the determined position and shape plans can be shown together with the roadmap on the display 12 and the control unit 4 can be adapted to provide a graphical user interface allowing the user to select one of the determined position and shape plans and to control the robotic device 2, 3 in accordance with the selected position and shape plan.

The control unit 4 may be adapted to allow the user to interrupt the automatic control of the steering unit 3. In particular, the control unit 4 may be adapted to control the steering unit 3 only, if the user inputs a signal indicating that the control unit 4 is allowed to control the steering unit 3 based on the roadmap, the target position and shape of the catheter 2 and the actual position and shape of the catheter 2. For instance, the control unit 4 can be adapted to control the steering unit 3 only, if a switch at the input unit 11 or another switch is pressed, wherein the control is interrupted, if the switch is not pressed. The switch may be a hand switch or a foot switch. If the robotic system is not automatically controlled, the user may control the position and shape of the catheter 2 by using the input unit 11, while the road map, the actual position and shape of the catheter 2 and the target region are shown on the display 12.

Figure 2:
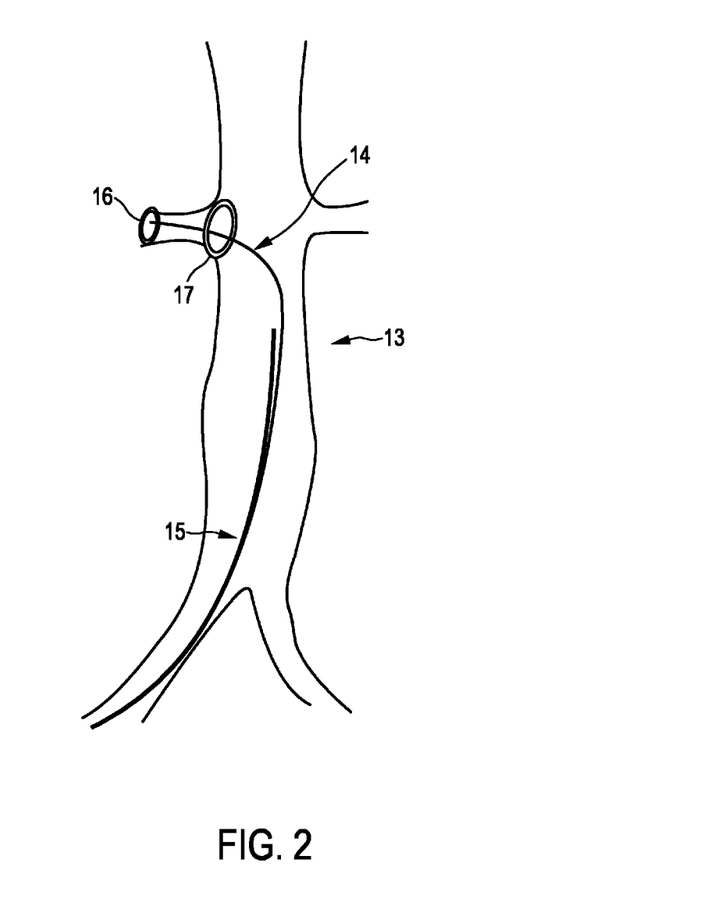

FIG. 2 illustrates schematically and exemplarily a roadmap 13 with two target rings 16, 17, through which the catheter 2 should be navigated, the target position and shape 14 of the catheter 2 and the actual position and shape 15 of the catheter 2.

Figure 3:
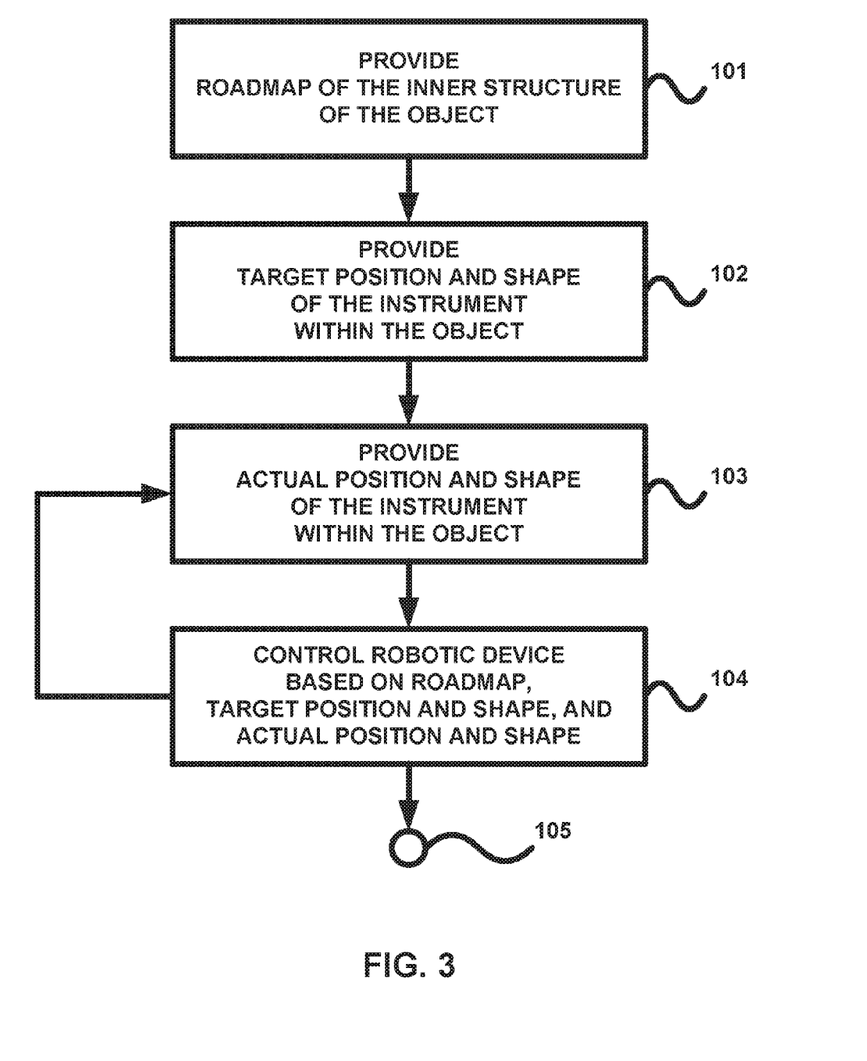
FIG. 3 shows a flowchart exemplarily illustrating an embodiment of a robotic method for moving the shapeable instrument within the person.

In the following an embodiment of a robotic method for moving a shapeable instrument within an object will exemplarily be described with reference to a flowchart shown in FIG. 3.

In step 101 the inner structure providing unit 5 provides the roadmap 13 showing the inner structure of the person 7 and in step 102 the target position and shape providing unit 9 provides the target position and shape 14 of the catheter 2 within the person 7. The target position and shape 14 can be provided, for instance, based on target rings 16, 17 and the roadmap 13 by the target position and shape providing unit 9. In step 103 the actual position and shape 15 of the catheter 2 within the person 7 is determined by the actual position and shape providing unit 10 by using OSS and in step 104 the steering unit 3 is controlled by the control unit 4 depending on the roadmap 13, the target position and shape 14 of the catheter 2 and the actual position and shape 15 of the catheter 2. Steps 103 and 104 are performed in a loop such that the control of the steering unit 3 can consider updated actual positions and shapes of the catheter 2 as a feedback. If the user interrupts the controlling process or if the catheter 2 has reached the target position and shape, the method ends in step 105.

The robotic system and method described above with reference to FIGS. 1 and 3 derive a target position and shape based on one or several targets, i.e. one or several target regions, and based on an anatomical constraint roadmap. The control unit 4, which can also be regarded as being a motor control, uses these inputs along with the continuously monitored actual position and shape, in order to navigate the catheter within the person with no or with only few user interactions. The few user interactions may include a modification of the target position and shape, an interruption of the motor drive, wherein the motor drive may only be enabled when a foot switch or a hand switch is continuously pressed, and restarting the target planning, i.e. restarting the determination of the position and shape plan.

The roadmap can be generated from pre- and/or intra-procedural medical data. To provide a safe control of the robotic system, the road map can have zones where strong force is inadvisable, for example, close to the inner walls, in areas of high tortuosity and in anatomically unsafe areas, i.e. in areas which are known to be easily damaged because of a known weakness.

The target position and shape can be derived from the planning information, i.e., for instance, from the input target region, from the roadmap or from another anatomical context in the same frame of reference. The target region can, for instance, be created by allowing a user to add targeting landmarks or rings to the roadmap or other anatomical data like medical images shown on the display 12, wherein a target position and shape can be plotted on the display 12 depending on the anatomical context, for instance, the roadmap or another anatomical information, and on the target region, for instance, the target rings.

The position and shape plan can be broken up into smaller steps defined by, for instance, longitudinal translation vectors and rotation angles. The longitudinal translation vectors can define in which direction and by which amount the instrument should be moved in the respective step and the rotation angles can define the rotations between respective portions of the instrument and the rotation of the entire instrument, which should be used in the respective step. For each intermediate step the corresponding motors can be actuated by the user and immediate feedback from the position and shape reconstruction, i.e. the actual position and shape of the instrument, can be used to compare the intermediate planned position and shape with the actual position and shape. If the intermediate planned position and shape differs from the actual position and shape by a given delta, the system may stop and recalculate. At all times the user can make corrections to the target position and shape, i.e. the final desired target position and shape, and also to the intermediate target position and shape, which should be obtained after the respective intermediate step has been performed, for example, by redefining it or choosing from alternatives. The user can also choose to halt the actuation.

Although in above described embodiments the shapeable instrument is a catheter, in another embodiment the shapeable instrument can also be another instrument like a needle. For a needle path the safety zones are preferentially defined by nerve tissue, fat tissue and/or vessels.

The robotic system can be adapted to navigate the shapeable instrument in any constraint environment, in particular, in any lumen within a person or an animal. For instance, the robotic system can be adapted to provide an endovascular, an endoluminal, a spinal cord, et cetera navigation.

Although in above described embodiments the target position and shape providing unit is adapted to determine the target position and shape based on the roadmap and the target region, in other embodiments the target position and shape providing unit may be adapted to allow a user to more directly define the target position and shape, i.e. not only by defining the target region. For instance, the target position and shape providing unit can be adapted to allow a user to add markers to a roadmap or another kind of image like a computed tomography image or a magnetic resonance image showing the inner structure of the person and to determine the target position and shape of the catheter within the person based on the added markers. For example, a user may add several markers, which can be automatically connected by the target position and shape providing unit for determining the target position and shape.

Although in above described embodiments a roadmap is provided as the inner structure of the person, wherein the roadmap may have been determined based on a medical image like a computed tomography image or a magnetic resonance image, which may have been acquired before the interventional procedure, in other embodiments the inner structure providing unit can also be adapted to provide, for instance, a live three-dimensional medical image like a live three-dimensional ultrasound image, which is acquired during the interventional procedure, wherein the control unit can be adapted to control the robotic device based on the inner structure shown in the live three-dimensional image, the actual position and shape of the instrument and the target position and shape of the instrument. This allows the control unit to consider changes of the inner anatomy of the person, which may be caused by the instrument within the person, during the interventional procedure.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the target position and shape, the provision of the inner structure, et cetera performed by one or several units or devices can be performed by any other number of units or devices. These procedures and/or the control of the robotic system in accordance with the robotic method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a robotic system for moving a shapeable instrument like a shapeable catheter within an object like a person. The system comprises a robotic device for modifying the shape of the instrument and moving the instrument within the object and a control unit for controlling the robotic device based on structure information like a roadmap, a target position and shape and an actual position and shape such that the instrument is moved and the shape of the instrument is modified from the actual position and shape to the target position and shape. Since the control unit considers structure information while controlling the robotic device, the navigation of the instrument can be automatically performed under consideration of knowledge about regions within the object, through which the instrument is navigatable. The navigation may therefore be performed without or with few user interactions only.

The invention claimed is:

1. A robotic system for moving a shapeable instrument within an object, the system comprising:
   a robotic device for modifying the shape of the instrument and moving the instrument within the object,
   an inner structure providing unit for providing structure information about the inner structure of the object,
   a target position and shape providing unit for providing a target position and shape of the instrument within the object,
   an actual position and shape providing unit for providing the actual position and shape of the instrument within the object, and
   a control unit for controlling the robotic device based on the structure information, the target position and shape of the instrument, and the actual position and shape of the instrument such that the instrument is moved and the shape of the instrument is modified from the actual position and shape to the target position and shape,
   characterized in that the inner structure providing unit is adapted to indicate safety zones within the inner structure, in which the robotic device should not apply forces larger than a predefined force value to the instrument for at least one of modifying the shape of the instrument and moving the instrument within the object, and
   further characterized in that the control unit is adapted to control the robotic device such that no forces are applied by the robotic device to the instrument in the safety zones larger than the predefined force value while the at least one of the shape of the instrument is modified and the instrument is moved from the actual position and shape to the target position and shape.

2. The robotic system as defined in claim 1, wherein the robotic system further comprises a target region providing unit for providing a target region to which the instrument is to be moved, wherein the target position and shape providing unit is adapted to determine the target position and shape of the instrument within the object based on the target region and the structure information.

3. The robotic system as defined in claim 1, wherein the target position and shape providing unit is adapted to allow the user to modify the target position and shape of the instrument.

4. The robotic system as defined in claim 1, wherein the inner structure providing unit is adapted to provide a structure image, which shows the inner structure, as the structure information and the target position and shape providing unit is adapted to a) allow a user to add markers to the structure image and b) determine the target position and shape of the instrument within the object based on the added markers.

5. The robotic system as defined in claim 1, wherein the control unit is adapted to control the robotic device only, if a user inputs a signal indicating that the control unit is allowed to control the robotic device based on the structure information, the target position and shape of the instrument and the actual position and shape of the instrument.

6. The robotic system as defined in claim 1, wherein the actual position and shape providing unit is adapted to provide the position and shape of the instrument by optical shape sensing.

7. The robotic system as defined in claim 1, wherein the actual position and shape providing unit and the control unit are adapted to provide a feedback loop during a movement of the instrument within the object, wherein the actual position and shape of the instrument is continuously updated and the robotic device is continuously controlled based on the structure information, the target position and shape of the instrument and the updated actual position and shape of the instrument.

8. The robotic system as defined in claim 1,
   wherein the inner structure providing unit and the control unit are adapted to provide a feedback loop during a movement of the instrument within the object, and
   wherein the inner structure of the object is continuously updated and the robotic device is continuously controlled based on the updated structure information, the target position and shape of the instrument and the actual position and shape of the instrument.

9. The robotic system as defined in claim 1, wherein the control unit is adapted to:
   determine a position and shape plan defining a modification of the shape and a movement of the instrument, which is required for arranging the instrument in accordance with the target position and shape, depending on the structure information, the target position and shape of the instrument and the actual position and shape of the instrument, and
   control the robotic device in accordance with the determined position and shape plan.

10. The robotic system as defined in claim 9,
    wherein the inner structure providing unit is adapted to provide a structure image, which shows the inner structure, as the structure information, wherein element weights are assigned to elements of the structure image, and
    wherein the control unit is adapted to determine the position and shape plan such that a plan weight, which depends on the element weights assigned to the elements of the structure image that correspond to regions within the object at least temporarily occupied by the instrument when performing the position and shape plan, is optimized.

11. The robotic system as defined in claim 9, wherein the control unit is adapted to determine several position and shape plans, wherein the system further comprises a display for displaying the determined position and shape plans together with the inner structure of the object as defined by the provided structure information and wherein the control unit is adapted to provide a user interface allowing the user to select one of the determined position and shape plans and to control the robotic device in accordance with the selected position and shape plan.

12. The robotic system as defined in claim 9,
wherein the position and shape plan defines planned intermediate positions and shapes of the instrument to be used while the shape of the instrument is modified and the instrument is moved from the actual position and shape to the target position and shape,
wherein the actual position and shape providing unit is adapted to continuously update the actual position and shape of the instrument while the shape of the instrument is modified and the instrument is moved in accordance with the position and shape plan, and
wherein, during the modification of the shape of the instrument and the movement of the instrument in accordance with the position and shape plan, the control unit is adapted to modify the position and shape plan based on the structure information, the target position and shape and the updated actual position and shape of the instrument responsive to a deviation between an expected planned intermediate position and shape of the instrument and the updated actual position and shape of the instrument being larger than a predefined threshold.

13. A robotic method for moving a shapeable instrument within an object, the method comprising:
providing structure information about the inner structure of the object by an inner structure providing unit,
providing a target position and shape of the instrument within the object by a target position and shape providing unit,
providing the actual position and shape of the instrument within the object by an actual position and shape providing unit,
controlling a robotic device, which is configured to modify the shape of the instrument and move the instrument within the object, based on the structure information, the target position and shape of the instrument, and the actual position and shape of the instrument by a control unit such that the instrument is moved and the shape of the instrument is modified from the actual position and shape to the target position and shape,
indicating safety zones within the inner structure, in which the robotic device should not apply forces larger than a predefined force value to the instrument for at least one of modifying the shape of the instrument and moving the instrument within the object, and
controlling the robotic device such that no forces are applied by the robotic device to the instrument in the safety zones larger than the predefined force value.

14. A non-transitory computer-readable storage medium in which computer-executable code is stored, the computer-executable code configured to cause a robotic system to:
provide structure information about the inner structure of the object,
provide a target position and shape of the instrument within the object,
provide the actual position and shape of the instrument within the object,
control a robotic device, which is configured to modify the shape of the instrument and move the instrument within the object, based on the structure information, the target position and shape of the instrument, and the actual position and shape of the instrument such that the instrument is moved and the shape of the instrument is modified from the actual position and shape to the target position and shape,
indicate safety zones within the inner structure, in which the robotic device should not apply forces larger than a predefined force value to the instrument for at least one of modifying the shape of the instrument and moving the instrument within the object, and
control the robotic device such that no forces are applied by the robotic device to the instrument in the safety zones larger than the predefined force value.

\* \* \* \* \*